United States Patent
Pardikes

(10) Patent No.: US 6,884,867 B2
(45) Date of Patent: Apr. 26, 2005

(54) PRECONDITION FOR INVERTING, MIXING, AND ACTIVATING POLYMERS

(75) Inventor: Dennis G. Pardikes, Palos Park, IL (US)

(73) Assignee: Norchem Industries, Mokena, IL (US)

( * ) Notice: Subject to any disclaimer, the term of this patent is extended or adjusted under 35 U.S.C. 154(b) by 99 days.

(21) Appl. No.: 10/369,011

(22) Filed: Feb. 19, 2003

(65) Prior Publication Data

US 2003/0156490 A1 Aug. 21, 2003

Related U.S. Application Data

(60) Provisional application No. 60/358,273, filed on Feb. 21, 2002.

(51) Int. Cl.$^7$ .......................... B01F 15/04; B01F 15/06; C08F 6/00
(52) U.S. Cl. ...................... 528/503; 366/144; 366/137; 366/162.1; 366/348; 422/132; 264/101; 137/7
(58) Field of Search ................ 366/136, 173, 366/144, 348, 349, 162.1; 422/132, 138; 528/480, 503; 264/101, 37.18; 425/200, 215; 137/10

(56) References Cited

U.S. PATENT DOCUMENTS

| | | | | |
|---|---|---|---|---|
| 3,242,150 A | * | 3/1966 | Scoggin | 528/503 |
| 3,402,161 A | * | 9/1968 | Norwood | 526/65 |
| 5,323,017 A | | 6/1994 | Pardikes | 250/573 |
| 5,372,421 A | | 12/1994 | Pardikes | 366/137 |
| 6,004,024 A | * | 12/1999 | Ho et al. | 366/167.1 |
| 6,384,109 B1 | * | 5/2002 | Witecki, Jr. | 366/136 |

* cited by examiner

Primary Examiner—Tony G. Soohoo
(74) Attorney, Agent, or Firm—Michael Best & Friedrich LLP

(57) ABSTRACT

A process for activating polymer including preconditioning a diluent by heating it to a high temperature and then mixing the heated diluent with the polymer to form a blend having a high polymer content (e.g., about 5% polymer and 95% hot diluent). The blend is activated and then diluted by mixing it with a cold or cool diluent in order to provide an output stream of about 0.25–2% polymer having a relatively low temperature. The high temperature and high polymer content enables a continuous process, as distinguished from batch processes used heretofore which required substantial holding time in an aging tank. The reduction of the temperature of the blend by mixing it with cold or cool diluent prevents damage to heat-sensitive polymers.

23 Claims, 3 Drawing Sheets

PRECONDITION FOR INVERTING, MIXING, AND ACTIVATING POLYMERS

This appln claims benefit of 60/358,273 Feb. 21, 2002.

This invention relates to means for and methods of inverting, mixing and activating polymers and, more particularly, to thermally preconditioning polymers especially—although not exclusively—for enabling the continuous production of activated polymers.

While a purist sometimes distinguishes between terms such as "activation" or "inversion" of a polymer, or the like, these are equivalent terms having the same meaning insofar as the following specification and claims are concerned. Likewise, the terms "water," "electrolyte," and "diluent" are equivalent terms insofar as the invention is concerned.

Reference is made to my U.S. Pat. Nos. 5,323,017 and 5,372,421 (the "patented process") which show some of the structures and processes described herein. These patents use a four-step process of (1) Premixing a polymer and a diluent, (2) blending the premixed polymer and diluent under pressure, (3) recycling a portion of the blended mix, and (4) suddenly relaxing the pressure of the blend as it is released from the blending and recycling steps. In general, this four-step process is an excellent procedure for activating most presently known polymers. However, there are two reasons for improving these systems.

First, although most polymers may be activated by some variation of the four-step process, there are many kinds of polymers which require variations or different procedures in order to activate them. In fact, there are polymers which have defied all efforts to activate them. Therefore, there is a need for new ways of implementing the four-step process.

Second, the four-step process has tended to be a batch-making process in which there was often a need to hold the polymer in an aging tank for an extended period of time while the polymer ages to reach the desired end product. This aging step is both expensive and time-consuming. Therefore, there is a need for a continuous process which reduces or eliminates the aging step.

Recent advances in emulsion polymer technology have moved the preferred method for activating from a batch/aging tank approach to direct in-line feeding. As a result, a thermal preconditioning approach is provided in the present invention to meet this need for direct in-line feeding. While the batch aging arrangement is still possible under the inventive thermal preconditioning process, the user now has an option of bypassing the aging tank altogether. The decision as to whether to exercise this option will depend largely upon the polymer that is being activated.

Accordingly, an object of this invention is to extend the basic four-step process to treat a great variety of different types of polymers. Here an object is to precondition the polymer so that a wider variety of polymers may be processed—some with and some without—the system and process shown in my above-referenced earlier patents.

Another object of the invention is to provide for activation of particular polymers which have heretofore stubbornly resisted efforts to activate them.

Yet another object of the invention is to provide a continuous activation system—as distinguished from a batch system—by enabling a steady flow of product, without requiring interruption for significant periods for aging separate batches of product.

Still another object of the invention is to provide an activation process which makes practical the creation of new activation polymers which were not considered heretofore because it was thought that they could not be activated, at least as a practical and economical matter.

In keeping with an aspect of the invention, these and other objects are accomplished by a process which consists of: (a) preheating a diluent to a temperature that is much higher than used heretofore; (b) using a mixture of polymer and diluent with a much higher percentage of polymers than has been used heretofore; (c) optionally activating the mixture by a use of the patented four-step process, as set forth in U.S. Pat. Nos. 5,323,017 and 5,372,421; and (d) diluting and cooling the activated mixture to a conventional ratio of polymer to diluent. The resulting process is run continuously at a relatively slow flow rate so that there is a proper amount of aging before the dilution step (d), thereby enabling a continuous production of activated polymer. Part of the slow flow process step may involve passage through a relatively small reservoir which delays the passage long enough for all of the aging that is necessary without interruption of the continuous production, so that a separate time-consuming aging step is not required.

A preferred embodiment of the invention is shown in the attached drawings, wherein.

Figure 1:
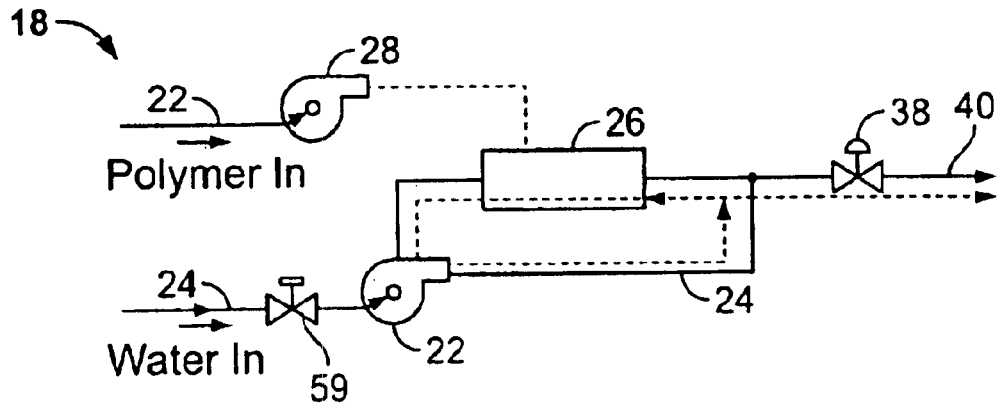
FIG. 1 shows a polymer activation system that uses the basic four-step procedure that is also shown and described in my above-referenced earlier patents.
Figure 2:
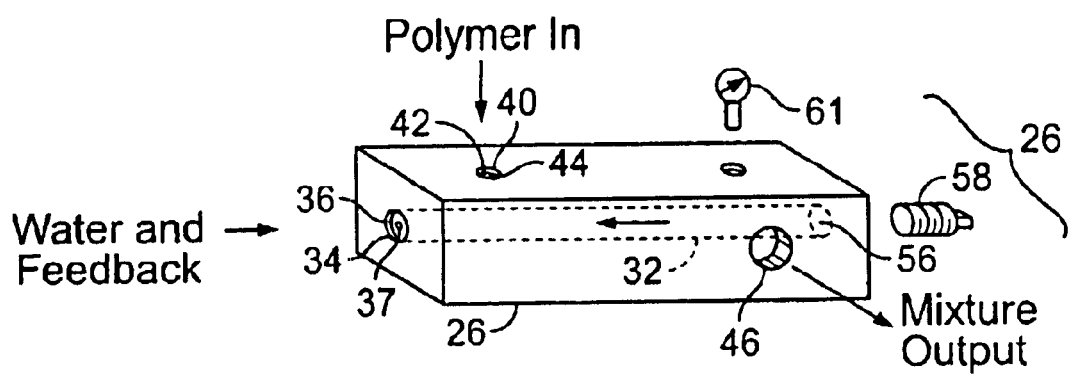
FIG. 2 shows a mixing block.
Figure 3A:
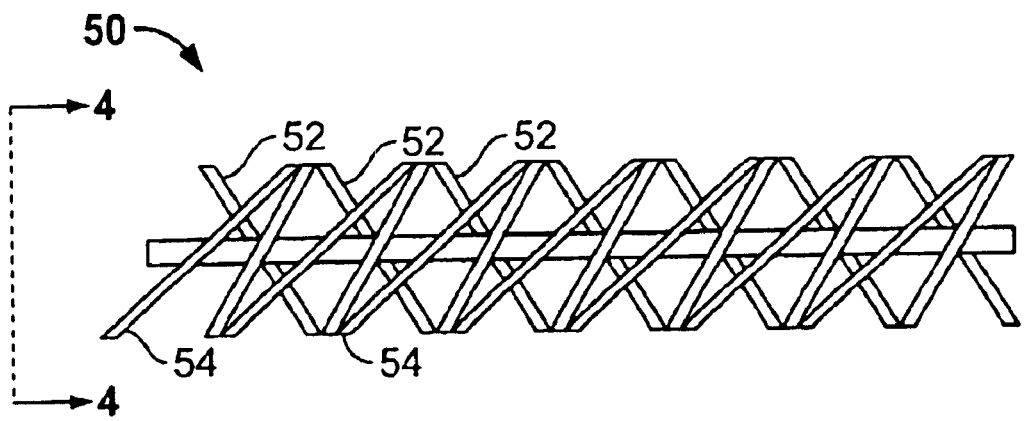
FIGS. 3A, 3B and 4 show a static mixer which is used both in the systems of my earlier patents and this invention, and at a downstream location of a continuous flow process enabled by this invention.
Figure 3B:
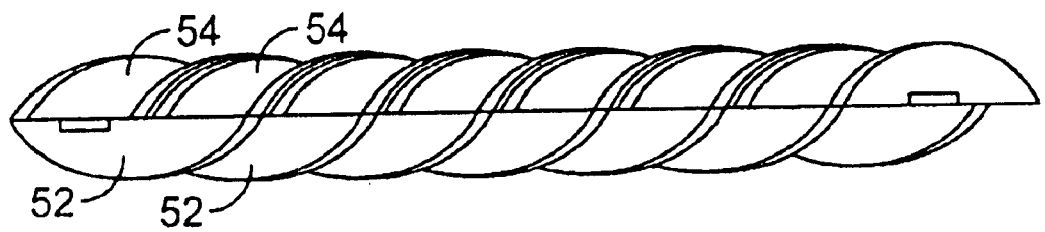

FIGS. 1–4 are taken from my U.S. Pat. No. 5,372,421.

Polymer processing systems 18 (FIG. 1) may take many forms. One example of a polymer processing system sold under the trademark "AnCAT" by Norchem Industries, 8910 West $192^{nd}$ Street, Mokena, Ill. 60448 is described below.

In the AnCAT process, a source 22 of neat polymer and a source 24 of a diluent or electrolyte (here water) are connected to a mixing block 26. The neat polymer source is coupled to mixing block 26 via pump 28. The water source is coupled to block 26 via a valve 59 and pump 22. As noted above, the terms "electrolyte," "diluent," and "water" are used interchangeably herein; however, it should be understood that all suitable materials are to be included within the scope of these terms.

The water and polymer are mixed at a relatively high pressure in mixing block 26, with a certain percentage of the mixed polymer and water being fed back and recirculated through a closed loop 24. The polymer flow is shown by dashed lines; the water by solid lines. Another percentage of the mixture is diverted through a pressure regulator 38 to a system output 40. The pressure regulator 38 produces a sudden and abrupt drop in pressure to cause a relaxation of the polymer molecules in the pressurized loop 24.

The AnCAT polymer processing system uses a combination of three elements which merge in the system of FIG. 1. These three elements are used for activating or inverting the polymers. The first element is provided by the pressure regulator 38 which abruptly drops the pressure, subjecting the pressurized polymer and water solution in feedback loop 24 to a sudden and violent drop in pressure as the solution passes through an orifice in regulator 38. The second element comprises subjecting the solution to a high flow and pressure condition through a static or motionless mixer in mixing block 26. The combination of variables governing the static mixer in mixing block 26 are believed to create Reynold's numbers sufficient for a satisfactory mixing. The third element comprises subjecting the solution to extreme three dimensional, hydrodynamic shear which is created within the chamber of a centrifugal pump/mixer 22 in feedback loop 24. In order to achieve satisfactory shear conditions, the pump/mixer combination requires an extraordinary input of energy, usually referred to as horsepower, as compared to the horsepower normally to be expected.

The mixing manifold 26 (FIG. 2) is, for example, a solid block of metal having a central bore 32 extending through substantially its entire length. The bore 32 stops short of a counterbored and threaded input opening 34, to form a bulkhead 36. An orifice 37 of fixed diameter is formed in the center of the bulkhead 36 to establish communication between the threaded input opening 34 and the central bore 32, with a flow rate that is controlled by the orifice diameter. The polymer solution experiences an extrusion type of shear as it passes through the orifice 37.

A first threaded hole 40 leads to another bulkhead 42 between the entrance to the counterbored and threaded hole 40 and the central bore 32. An orifice 44 is formed in the bulkhead 42 to establish communication and to control the flow rate between the hole 40 and the central bore 32.

The output port 46 is in direct communication with the central bore 32 to give an unimpeded outflow of a mixture of polymer and water.

Figure 4:
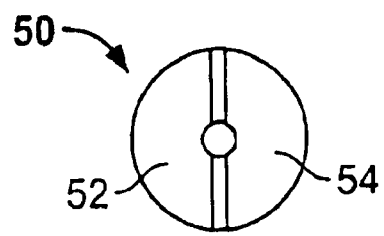

A static mixer 50 (FIGS. 3, 4) comprises two sets of semi-elliptical baffles which are set at an angle with respect to each other so that the overall end view configuration is a circle (FIG. 4). The baffles 52 (FIG. 3A) on one side of the static mixer are a series of spaced parallel plates. The baffles 54 on the other side of the static mixer are joined on alternate ends to give an overall zig-zag appearance. The outside diameter of the static mixer corresponds to the inside diameter of central bore 32. Therefore, the static mixer 50 slides through an end opening 56 and into the bore 32. Thereafter, a plug 58 seals off the end of the bore. In one embodiment, the static mixer 50 is a standard commercial product available from TAH Industries of Inlaystown, N.J.

The diluent (here, water) is introduced through the centrifugal pump 22 and into the mixing loop 24 (FIG. 1). The flow of water is controlled and metered by the throttling flow valve 59 (FIG. 1). The beginning stages of activation (the "preblend" stage) occurs inside the centrifugal pump assembly 22.

The centrifugal pump 22 is a modified commercial item which is derated on the high end of its output flow by a factor on the order of 2 to 7, for example, for most applications. On the low end of its output flow, the derating factor may be much higher. That is, the diameter (for example) of the impeller is trimmed to give a derated performance wherein there is a larger amount of stirring and mixing per volume flow, as compared to what might normally be expected from a standard commercial centrifugal pump. Other techniques for derating an impeller include verifying the pitch of the blades, thinning the width of the blades, and the like.

Derating is also controlled by an adjustment of the water inlet flow. In greater detail, by way of example, a centrifugal pump usually has a series of flow charts which are supplied by the manufacturer. One flow chart, which may be the one normally used, may describe how the pump could provide a flow of 20 gallons per minute to the top of a 40-foot head, for example. Another flow chart may describe how the same pump could be operated at a different speed to provide five times that capacity, or at 100 gallons per minute to the same 40-foot head, in this particular example.

The ratio of polymer to diluent admitted at inputs 22, 24, varies with the type of polymer being activated. With my previous systems, the ratio was generally less than or equal to about 1% polymer, although the ratio could vary as much as about 0.25–15%, depending upon the type of polymer. Nevertheless, it has been found that heretofore some polymers would not activate satisfactorily even with variations of the ratio and other system parameters.

I have found for these and similar hard-to-activate polymers, that the secret of a successful activation lies in the input temperature when activation actually begins. Moreover, with the proper temperature, the concentration of polymer in the diluent may be increased substantially, which enables a reduction in flow rate, making a continuous process possible.

Figure 5:
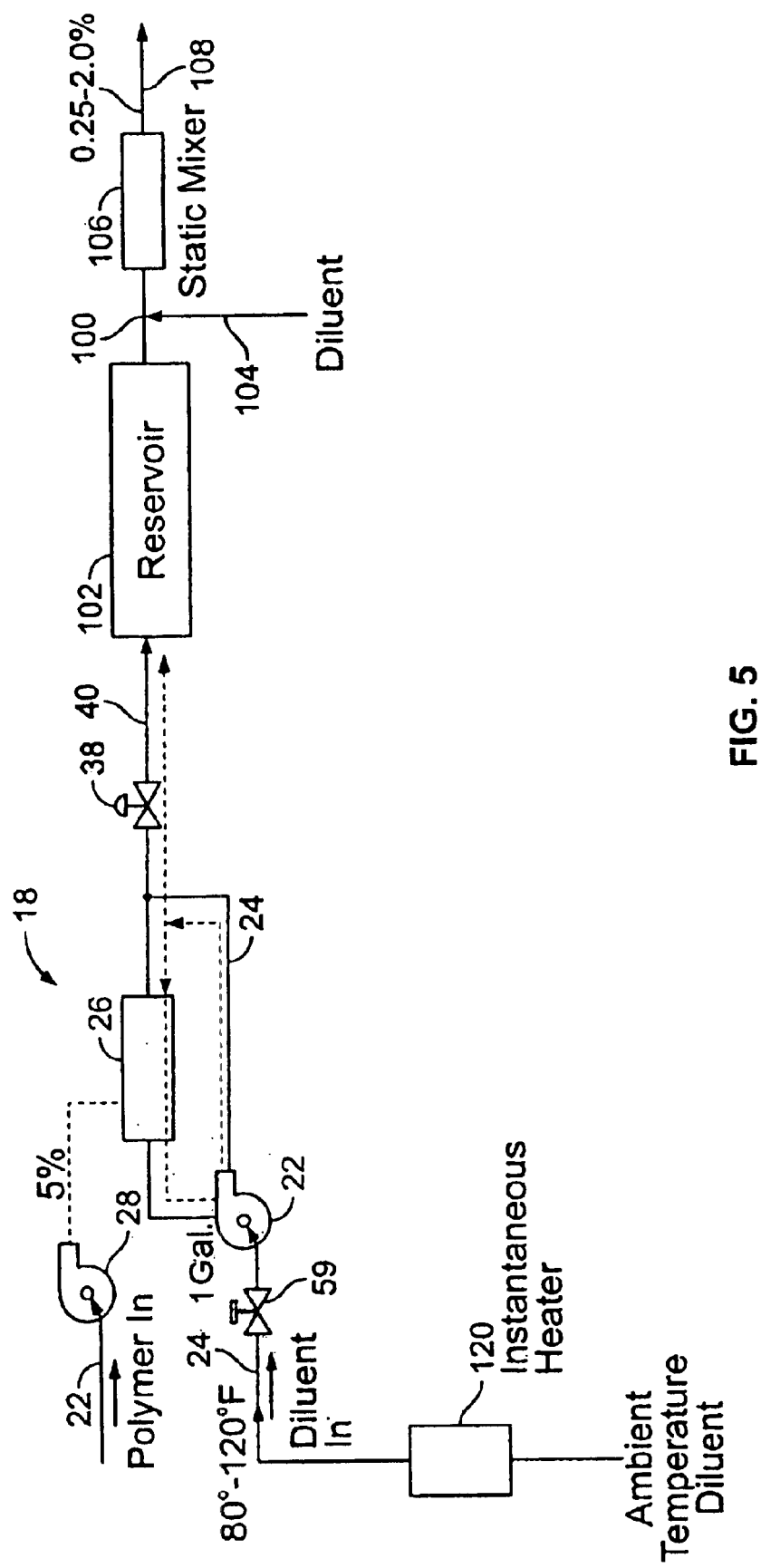
FIG. 5 illustrates the process of the present invention generally in block diagram form.

FIG. 5 shows my inventive system where the concentration of polymer to diluent (here, water) input is about 5% polymer, 95% water, although a range of about 2–7% polymer to the balance diluent may be used depending on the polymer being processed. For the type of polymer being described, the prior art concentration would have been on the order of about 0.25–1% polymer. Therefore, in the present invention the ratio of the polymer to water has been increased on the order of 5–20 times over that used in the prior art systems.

The foregoing description focused on joining my new thermal preconditioning step to the four-step polymer processing system shown in my U.S. Pat. Nos. 5,323,017 and 5,372,421. This concept may be broadened to use the thermal preconditioning as a stand alone process. As new polymers develop they may not require my prior patented processing, but can benefit from a form of my new thermal preconditioning approach.

The temperature of the diluent at the input 24 has been raised to a preselected temperature in the range of about 80°–180° F. and preferably about 80°–120° F. Heretofore, the corresponding range might have been about 40°–70° F., depending upon the type of polymer being processed; therefore, it is fair to say that the outflowing stream at 100 is both hot and has a high percentage of polymer, as compared to the conventional temperature and polymer concentration.

The high temperature accelerates the reaction of the polymer so that a higher percentage of polymer may be processed much more quickly than heretofore. As a result, the volume or rate of the outflow of the polymer diluent blend may be reduced significantly at output 40. In one example, a rate on the order of about one U.S. gallon per minute was used. However, a rate of about 0.5 to 4 gallons per minute could be used.

A reservoir 102 may be provided in the output line to further slow the discharge of the activated polymer. When a specific polymer does not require my entire previously patented four-step process, this output 24 may be connected to the reservoir, thereby bypassing some or all of this intermediate equipment. The amount of equipment that is bypassed depends upon the polymer that is being activated.

In one example, the reservoir 102 holds one U.S. gallon. However, a reservoir with a storage capacity of about 0.5 to 20 gallons could be used with the above outflow rate of about 0.5 to 4 gallons per minute. With this combination of high temperature, slow flow rate, and a brief delay in reservoir 102, there is enough time for full polymer activation and no need for the batch holding time required heretofore for aging the activating polymer. Instead, the invention enables polymer activation by a continuous process, which greatly reduces costs.

The heat for the inflowing water at 24 is preferably supplied by an instantaneous water heater 120 (FIG. 5). This type of heater detects flowing water which occurs when a demand for hot water is placed upon the system. On the demand for hot water, the heater 120 comes on and heats the stream of flowing water to a preselected temperature which may be set by adjustment of a suitable thermostat. There is no need for storing a tank of hot water. These instantaneous water heaters are readily available, standard commercial items.

Because of the use of instantaneous heater 120 and the continuous slow flow process using a limited size reservoir 102, there is no need for heating and storing a large volume of water. As a result, the invention provides a substantial savings in energy costs.

However, for most polymers, the outflowing stream of blended polymer and diluent either has too heavy a concentration of polymer to be completely useful, or the polymer cannot withstand a high temperature for an extended a period of time. Therefore, after the outflowing stream leaves the reservoir 102, a cool secondary stream 104 of diluent is introduced, at 100, into the blend of polymer and diluent. Enough of this diluent is injected into the outflowing stream to reduce the temperature and the concentration of the polymer to a range of about 0.25–2.0%, for example, which is the useful range for most follow-on manufacturing steps using the activated polymer.

The outflowing diluted stream may be sent through a static mixer 106 (similar to the static mixer of FIGS. 3A, 3B, 4) which insures a homogenous outflowing stream at the system output 108. This stream can be fed directly to an in-line process or temporarily stored in a use tank. Beyond that point, the blend goes to an end user who might, for example, use the blend in papermaking, wastewater treatment, mining applications, or the like to make a suitable final product, such as paint, plastic, or the like.

At output 108, the resulting end product of the system of FIG. 5 is substantially the same as the corresponding end product from the prior art system of FIG. 1. However, the nature of some polymers is such that the system of FIG. 1, and other prior art polymer activating systems, either could not activate altogether or could not satisfactorily activate these polymers.

I anticipate that not all new polymers will require the prior patented four-step process but can benefit from a form of my new thermal preconditioning process. An example might be a polymer pumped directly from the heat drum into a machine that simply disperses and preheats the solution at high concentration, holds it for a minute or two, secondarily dilutes it with cold water to bring it down to a usable concentration and feeds it directly in-line to the process. This type of polymer would not require the more elaborate four-step processing, but would benefit from the thermal preconditioning process. An additional example might be a polymer which due to a differing chemical makeup, requires more formal processing like the aforementioned "AnCat" system, but would also benefit from the thermal preconditioning approach which allows it to bypass the aging tank, thereby providing more direct feed advantages.

Recent testing of the thermal preconditioning process has uncovered another interesting fact. If the polymer solution is held too long at elevated temperatures, the polymer may become less efficient. This may be due to the rapid hydration of the polymer while maintained at higher temperatures. This hydration may prematurely rupture or alter the chemical bonds in the polymer reducing the reactivity of the polymer molecule, thereby negating the positive effects of thermal preconditioning. The answer to this seems to be to limit the time the polymer is exposed to the higher temperatures by following immediately by dilution with cold water. This dilution of the polymer with cold water eliminates further concern of thermal degradation. Below are some test results of my invention.

Time Exposure Effects Under High Temperatures
Buckman 5452 0.5% Concentration 2.5% Clay Slurry Settling Test

| AGING IN MINUTES | TEST |
| --- | --- |
| 0 | 1:25 |
| 1 | 1:26 |
| 6 | 1:49 |

Note:
shorter times indicate better performance.

The foregoing description focused on joining my new thermal preconditioning concept to the polymer processing system shown in my U.S. Pat. Nos. 5,323,017 and 5,372,421. This may be broadened to the use of my new thermal preconditioning approach as a stand alone process. As new polymers develop they may not require the prior patented processing, but can benefit from a form of my thermal preconditioning approach.

The advantages of the inventive system are (1) an ability to process some polymers which have heretofore defied satisfactory processing, (2) an ability to provide a polymer activation system having a continuous flow process as distinguished from the batch process used heretofore, (3) the ability to use an in-line instantaneous heater which enables a hot diluent at the desired temperature without requiring the heating and holding of a tank of hot diluent, (4) a reduction in cost over previous systems which required holding tanks and associated equipment for batch processing, and (5) general improvements over previous polymer activation systems, and general improvement of the end product.

Those who are skilled in the art will readily perceive how to modify the invention. Therefore, the appended claims are to be construed to cover all equivalent methods and structures which fall within the true scope and spirit of the invention.

What is claimed is:

1. A polymer activation method comprising the steps of: preheating a diluent to an elevated temperature; carrying out a four-step activation process comprising the steps of (a) premixing a polymer and said preheated diluent, with said polymer having an elevated concentration of polymer to diluent, (b) blending the premix to a predetermined pressure in a derated centrifugal pump, (c) recycling a first portion of the blended mixture at said predetermined pressure, and (d) suddenly reducing said pressure to relax the polymer in a second portion of the blended mixture; diluting said relaxed mixture to produce both a temperature lower than said elevated temperature and a reduced concentration of polymer to diluent; and passing said relaxed and diluted mixture through a mixer to an output.

2. The method of claim 1 wherein said elevated concentration of said polymer is in the range of about 2–7% polymer to 93–98% diluent.

3. The method of claim 1 wherein the elevated concentration of the blend is about 5% of said polymer and 95% of said diluent.

4. The method of claim 1 in which the preheating step is carried out by supplying the diluent through an instantaneous heater prior to said premixing step (a).

5. The method of claim 1 wherein said preheating of said diluent is to a temperature in the range of about 80°–180° F.

6. The method of claim 1 wherein said preheating of said diluent is to a temperature in the range of about 80°–120° F.

7. The method of claim 1 including the added step of slowly passing an outflow from said four-step activation process through a reservoir, the speed of said slow passage and the size of said reservoir being selected to provide continuous polymer activation.

8. The method of claim 7 wherein said slow speed of said passage is in the range of about 0.5 to 4 gallons per minute and said reservoir has a storage capacity in the range of about 0.5 to 20 gallons.

9. The method of claim 7 wherein said slow speed of said passage is about one gallon per minute and the capacity of the reservoir is about one gallon.

10. The method of claim 1 wherein said dilution of said relaxed mixture is at about 0.25–2.0% polymer to 98–99.75% diluent.

11. A system for activating polymer comprising: means for preheating a diluent to a high temperature; means for blending said heated diluent and a neat polymer in a pressurized loop, said blend having a high concentration of polymer to diluent; means for removing a portion of said blend from said pressurized loop; regulator means for subjecting said removed portion of said blend to a sudden and abrupt reduction of pressure; means for slowly conveying said blend from said regulator means through a reservoir, said speed of said slow conveyance and the size of said reservoir being chosen to retain said blend for a period of time being adequate to activate said polymer whereby said activation is a continuous process; means for diluting said blend issuing from said reservoir to reduce said high concentration of polymer to a useful concentration range; and means for mixing said diluted blend to produce a homogenous mixture of polymer to diluent.

12. The system of claim 11 wherein said preheating means is an instantaneous heater.

13. The system of claim 11 wherein said high temperature is in the range of about 80°–120° F.

14. The system of claim 11 wherein said high concentration of polymer is about 3–7% polymer to about 93–97% diluent.

15. The system of claim 11 wherein said high concentration is about 5% polymer to 95% diluent.

16. The system of claim 11 wherein said dilution of said blend is at about 0.25–2.0% polymer to 98–99.75% diluent.

17. The system of claim 11 wherein said means for mixing said diluted blend is a static mixer.

18. A continuous process for activating polymer comprising the steps of heating a diluent to a relatively high temperature; blending neat polymer into said high temperature diluent at a concentration of about 5% polymer to 95% diluent, said blending occurring at a relative slow speed which completes said activation during a continuous process; diluting said blend to a concentration of about 0.25–2.0% polymer to 98–99.75% diluent; and mixing said diluted blend to produce a homogeneous outflow.

19. The process of claim 18 wherein said relatively slow speed is achieved by moving said blend through a reservoir and on to said mixing step.

20. The process of claim 18 wherein said high temperature is about 80°–120° F. and said diluent is cold water.

21. A process for continuously activating polymer, said process comprising:

thermally preconditioning a diluent to a relatively high temperature of about 80°–180° F.;

mixing said heated diluent with polymer to form a blend having a high content of neat polymer in the concentration of about 5% polymer and 95% diluent;

activating said blend of polymer and diluent by a relatively slowly flowing stream during a period of time required to activate said polymer;

diluting the activated blend to provide an output stream having polymer in the range of about 0.25–2% polymer; and operating a system continuously to process said polymer.

22. The process of claim 21 further comprising the step of directing said stream through a reservoir for delaying a continuous outflow of said stream for a period which is long enough for activation of said polymer.

23. The system of claim 22 where said diluent is cold water.

* * * * *